United States Patent [19]

Shaffer et al.

[11] 4,326,515
[45] Apr. 27, 1982

[54] ENDOTRACHEAL TUBE RETAINER

[76] Inventors: Mark A. Shaffer, 5455 N. Sheridan Rd., Chicago, Ill. 60640; Frank J. Baker, II, 456 Poplar, Elmhurst, Ill. 60126

[21] Appl. No.: 140,175
[22] Filed: Apr. 14, 1980
[51] Int. Cl.³ .......................................... A61M 25/02
[52] U.S. Cl. ........................ 128/207.17; 128/DIG.26
[58] Field of Search ...................... 128/200.26, 202.28, 128/136, 207.14, 207.15, 207.16, 207.17, 207.18, 207.11, 348, 349 B, DIG. 26

[56] References Cited

U.S. PATENT DOCUMENTS

| | | | |
|---|---|---|---|
| 3,139,088 | 6/1964 | Galleher, Jr. | 128/136 |
| 3,774,616 | 11/1973 | White et al. | 128/DIG. 26 |
| 3,924,636 | 12/1975 | Addison | 128/207.14 |
| 3,946,742 | 3/1976 | Eross | 128/207.17 |
| 3,972,321 | 8/1976 | Proctor | 128/348 |
| 3,976,080 | 8/1976 | Bornhorst et al. | 128/DIG. 26 |
| 4,015,608 | 4/1977 | Rogers | 128/207.17 |
| 4,090,518 | 5/1978 | Elam | 128/207.15 |

FOREIGN PATENT DOCUMENTS 928035  5/1962  Denmark ...................... 128/200.26

OTHER PUBLICATIONS

Applebaum and Bruce, Saunders Publishers, 1976, *Endotracheal Intubation*, pp. 68 and 69.
Rusch, Inc., "Rusch Endostat" Literature.

*Primary Examiner*—Henry J. Recla
*Attorney, Agent, or Firm*—Hume, Clement, Brinks, Willian & Olds, Ltd.

[57] ABSTRACT

A retainer holds an endotracheal tube securely in a patient's mouth and prevents significant movement within the trachea. The retainer combines a member which is inserted in the patient's mouth and is adapted to receive and securely hold the tube within the tracheal lumen and a strap which encompasses the patient's head and fixes the member holding the tube securely within the patient's mouth.

21 Claims, 12 Drawing Figures

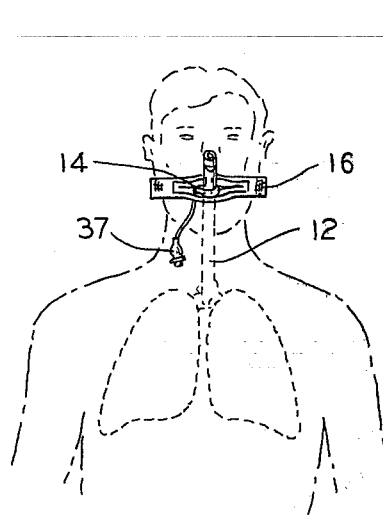
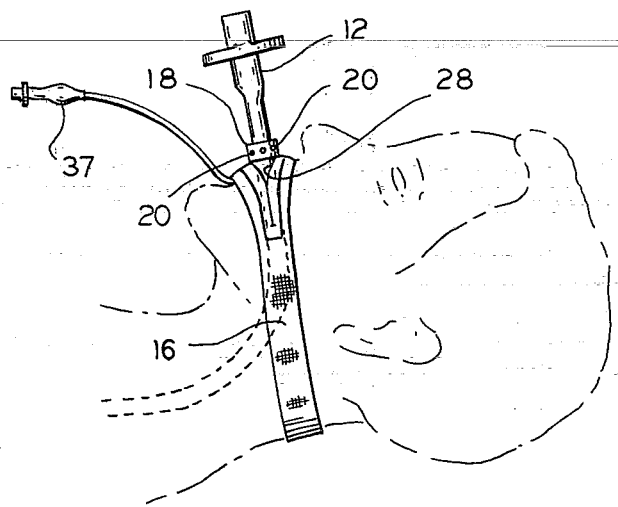
FIG.3  FIG.4
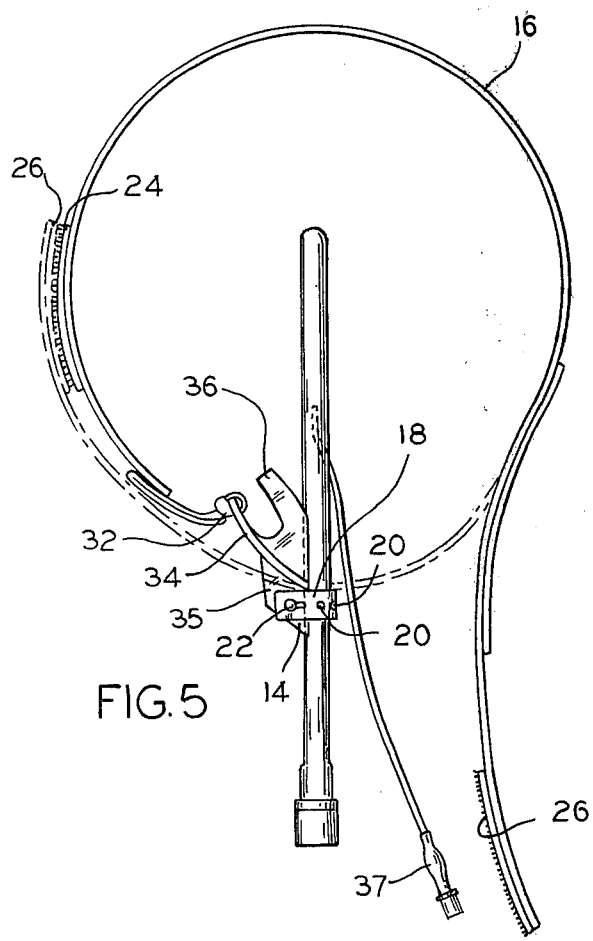
FIG.5
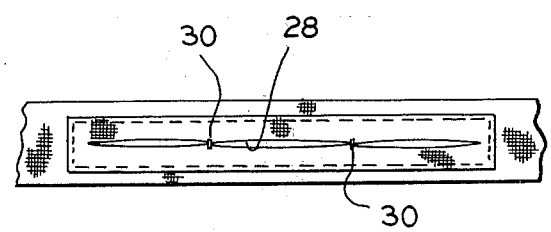
FIG.6
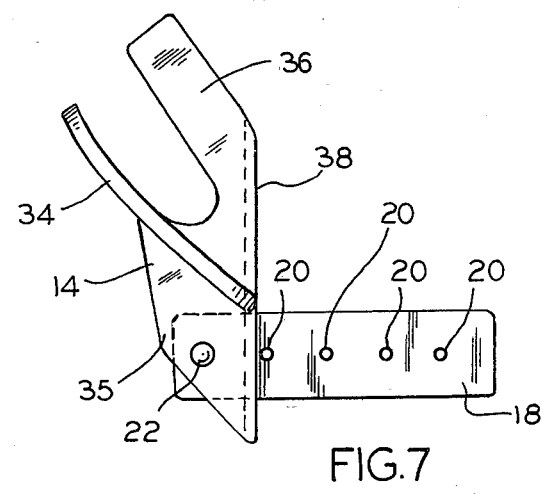
FIG.7

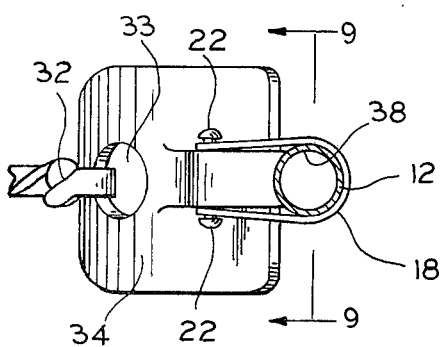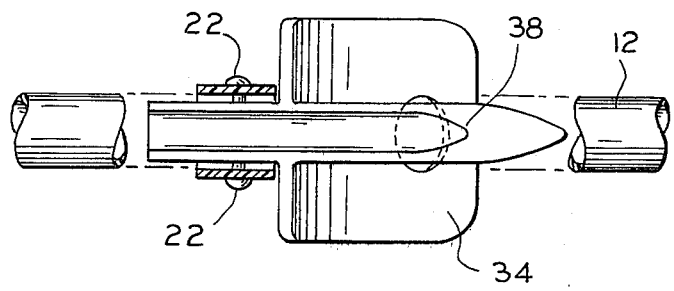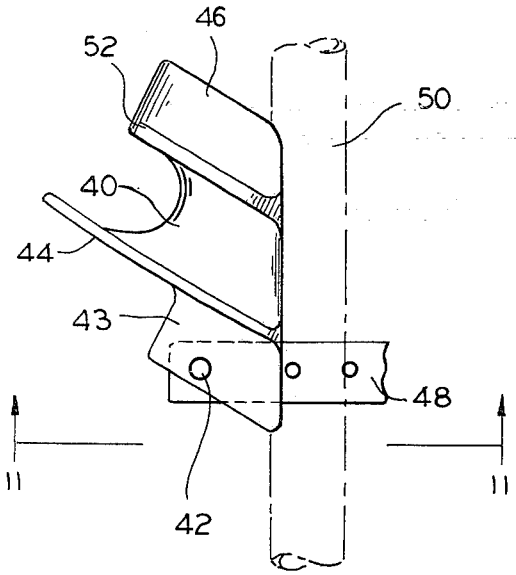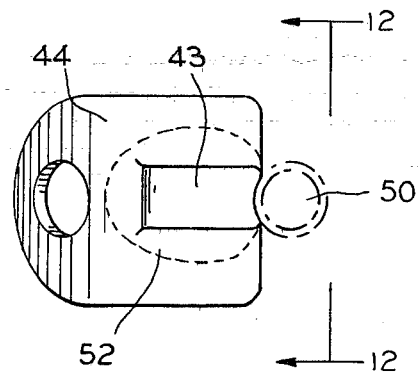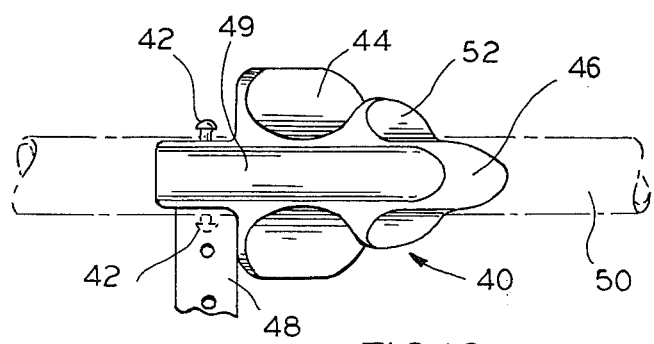

ENDOTRACHEAL TUBE RETAINER

BACKGROUND OF THE INVENTION

This invention relates to a device which holds endotracheal tubes securely within the patient's tracheal lumen. Endotracheal tubes are usually used to provide a temporary air passage between the lungs and atmosphere when the mouth, throat, or trachea are obstructed. Secure fixation of the endotracheal tube is important to prevent the accidental displacement of the tube from the tracheal lumen, resulting in possible asphyxiation, and to minimize damage to the mucous membrane of the larynx and trachea caused by rubbing of the tube against the membrane. The tube may be moved unintentionally, such as by a shift in the patient's position, by movement of the ventilating equipment or slippage due to inadequacy of current methods of securing the endotracheal tube.

Heretofore, such tubes were usually secured by taping the tube to the facial skin of the patient around the mouth or nose. A number of problems occur when this method is used. For example, tape does not always securely retain the tube in its proper position, and it is often necessary to use tincture of benzoin in conjunction with the tape to provide a stronger bond. However, benzoin often irritates the patient's skin. Sometimes it is necessary to use paper tape, rather than the standard adhesive tape, on patients with highly sensitive skin or allergies to standard adhesive tape. After taping the tube, accidental displacement of the tube may still result from spontaneous movement of the endotracheal tube of the patient or the ventilator. This unwanted spontaneous movement of the endotracheal tube is promoted by the mucous secretions of the patient and the inability of adhesive tape to hold under these conditions. When the movement of the endotracheal tube occurs, readjustment of the tube is often necessary to insure proper ventilation of both lungs. This will require cleansing of the patient and the endotracheal tube and subsequent retaping. Movement of the tube may be so great as to constitute total dislodgement from the trachea in which case the patient is in immediate danger of respiratory arrest. Such an occurence requires complete re-intubation of the patient with all of its attendent risks, such as damage to the oro-pharynx and trachea and esophageal intubation.

A further problem occurs if the person performing the taping lacks extensive experience. A well-trained person will take 2 to 3 minutes in taping the tube in an emergency situation, whereas someone with less experience needs a much longer period to properly tape the tube in place. Often, the time spent in this task is critical to the well-being of the patient, and a speedy insertion and affixation of the endotracheal tube may mean the difference between life and death.

A further problem occurs when a patient may bite the endotracheal tube. This is sometimes prevented by the use of a plastic oral airway which itself needs to be taped into place. The result of a patient biting the endotracheal tube may be the occurrence of an air leak which may result in the ventilator supplying an inadequate amount of oxygen to the patient.

Accordingly, an object of this invention is to provide a safe and expeditious method and device for initially fixing an endotracheal tube so as to minimize the movement of that tube. Another object is to provide a method and device which can be efficiently used by those who are inexperienced in the art of endotracheal tube fixation. A further object of this invention is to provide a method and device which will allow for expeditious readjustment of the tube when necessary. A further object of this device is to provide an integral bite lock to prevent perforation or obstruction of the endotracheal tube through biting of the patient.

Further objects will be apparent from the description, drawings and claims.

SUMMARY OF THE INVENTION

In keeping with one aspect of the invention, a block member of semi-hard plastic, i.e., plastic which has elasticity, but will maintain its form, is molded with a groove or channel along one side. The groove is adapted to receive an endotracheal tube. Along the block's lower side, a bite plate is formed which will fit between the patient's upper and lower teeth or upper and lower gingiva and preclude the patient from inadvertently closing his mouth and thereby obstructing or perforating the endotracheal tube. Near the top of the block and projecting from either side of the groove are knobs or projections which can engage an elastic band containing a plurality of apertures. The band clamps the endotracheal tube firmly within the groove in the block member. A tie plate extends from the middle of the block opposite the groove and is contoured to fit against the outer surface of the patient's mouth and cheek. An elastic strap containing a medial slit is removably connected to the tie plate, and the strap encompasses the patient's head over the mouth so that the endotracheal tube and block project through it. The strap is secured about the patient's head by an appropriate fastener.

The above mentioned and other features of the invention and the manner of obtaining them will become more apparent, and the invention itself will be best understood by reference to the following description of the invention in conjunction with the accompanying drawings.

BRIEF DESCRIPTION OF THE DRAWINGS

FIG. 3 is a reduced front plan view of the embodiment of FIG. 1 showing the manner in which the tube is inserted in a patient's trachea.

FIG. 4 is a left side plan view of the embodiment of FIG. 1.

FIG. 5 is a plan view of the embodiment of FIG. 1, showing the inventive device when it is not attached to a patient.

FIG. 6 is a partial top plan view of one of a number of types of the straps which may be used in the embodiment of FIG. 1.

FIG. 7 is a side plan view of the block portion of the embodiment of FIG. 1.

FIG. 8 is a top view of the block and tube of the embodiment of FIG. 1, the tube being shown in cross section.

FIG. 9 is a side view of the block and a portion of the tube of the embodiment of FIG. 1 in which the tube is shown in partial cross section.

FIG. 10 is a side view of the embodiment of a second embodiment of the invention showing the block and a portion of the tube.

FIG. 11 is a bottom view of the second embodiment of the invention taken along line 11—11 of FIG. 10.

FIG. 12 is a side view of the second embodiment of the invention taken along line 12—12 of FIG. 11.

DETAILED DESCRIPTION OF THE INVENTION

Figure 1:
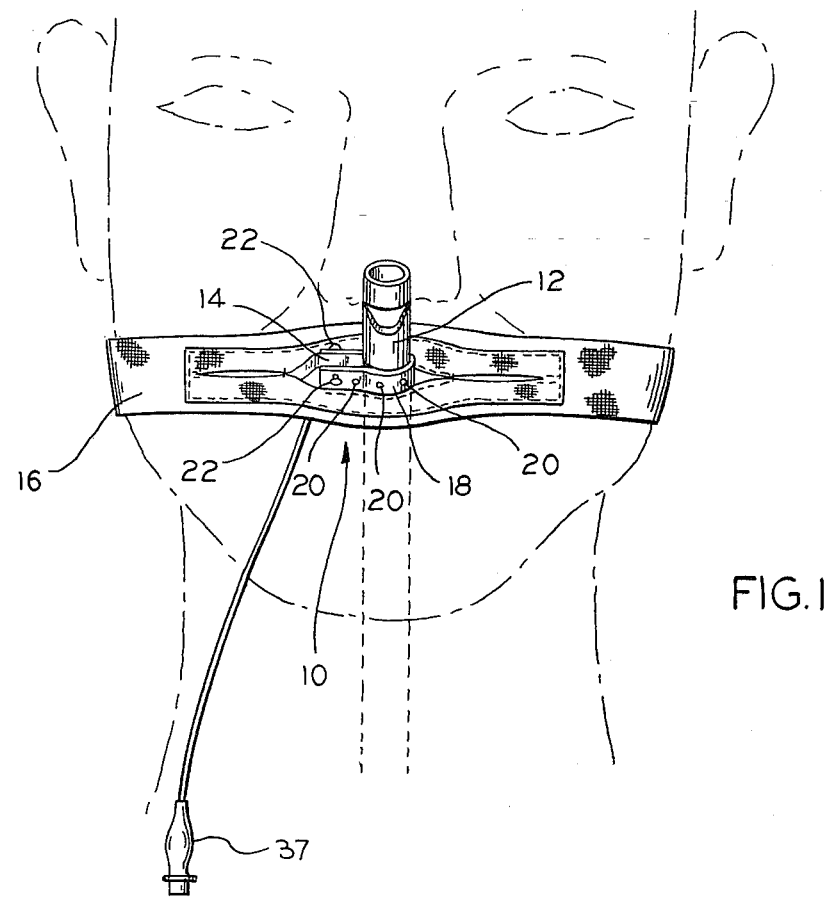
FIG. 1 is a front plan view of one embodiment of the invention as applied to a patient.
Figure 2:
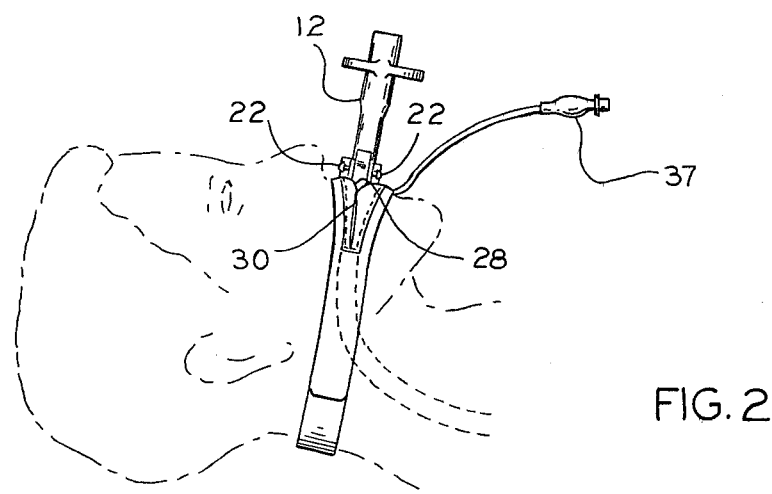
FIG. 2 is a right side plan view of the embodiment of FIG. 1.

FIGS. 1-9 show the preferred embodiment of the invention. Retainer 10 secures endotracheal tube 12 to a patient. The retainer 10 comprises a block member 14, head strap 16, and a band 18. The member 14 is preferably made from a soft, moldable plastic. As best shown in FIGS. 5 and FIG. 7, member 14 includes a tie plate 34, a bite plate 36 beneath tie plate 34, and a flange 35 above plate 34. Tie plate 34 is curved to rest along the outside of the patient's cheek and contains an opening 33 through which the strap 16 may be secured. Bite plate 36 extends below tie plate 34 to permit insertion of the bite plate between the patient's upper and lower teeth or gums and is suitably wide to prevent the patient from inadvertantly occluding or perforating the tube by biting. It has been found, however, that the bite portion 36 does not have to be as wide as the diameter of tube 12. Projections 22 extend from flange 35, and flange 35 provides a base against which band 18 secures tube 12. The projections 22 may be metal screws, molded portions of the plastic block, or other suitable extensions from the flange.

Member 14 also contains a groove 38 along one edge which is rounded to receive the endotracheal tube, as best shown in FIGS. 5, 8 and 9. Endotracheal tubes range in size from 6 millimeters to 10.5 millimeters in internal diameter for adults, and are smaller for children. The rounded groove 38 provides an seat for the tube when secured to member 14 by band 18.

Band 18 contains a plurality of co-linear apertures 20. Preferably, the band 18 is made of an elastic, nonskid material, such as latex. Band 18 is of a length, width and thickness which will provide an adequate restraining force against the endotracheal tube with only a minor distortion in the band. In the preferred embodiment, the band is approximately two and one-quarter inches long (while under no tension), five-eighths inches wide, and one-sixteenth inches thick. The apertures 20 are sized to fit over the two projections 22 which are located on opposing sides of member 14. When the tube 12 is properly held within block 14, band 18 stretches over the endotracheal tube 12 and is secured at its ends to block 14 by the projections 22 passing through apertures 20. The elastic deformation of the band holds the endotracheal tube firmly to member 14. The appropriate apertures 20 to be impaled by projections 22 depend upon the diameter of the endotracheal tube.

The preferred embodiment for the head strap 16 comprises an elastic strap and a two-part hook and loop fastener, commercially known under the trademark Velcro. The first part 24 of the fastener is attached along a mid-portion of the strap 16, and the second part 26 of the fastener is attached at one end of strap 16, as best shown in FIG. 5. The two parts 24 and 26 of the fastener can be joined to form strap 16 into a loop. In FIG. 6, a medial portion of the strap is shown wherein an opening or slit 28 runs through a length of the strap. Preferably, this opening is reinforced with an absorbant cloth to reduce irritation of the patient's skin. The opening 28 is divided into sections by darts 30, thereby providing a number of openings through which the top of member 14 and endotracheal tube 12 may fit. Fixed at the opposite end of strap 16 from the fastener 24 and 26 is a cloth lace 32 for attaching the strap 16 to the tie plate 34 through the opening 33 in plate 34.

When in use, the strap 16 surrounds the patient's head and is positioned so that opening 28 is situated over the patient's mouth. The endotracheal tube 21 and member 14 are inserted through one of the sections in the opening 28 defined by the darts 30 as selected by the physician, depending on the size of the patient's head and neck. An endotracheal tube cuff inflator 37 attached to tube 12 is shown in FIG. 4 passing under strap 16. The cuff inflator 37 is used to inflate a cuff (not shown) located near the internal or inserted end of the tube to prevent vomitus from entering an air passage.

FIGS. 10, 11 and 12 show another embodiment of the invention. FIG. 10 shows member 40 which comprises projections 42 extending from flange 43, an apertured tie plate 44, and bite plate 46. An apertured elastic band 48 is also provided to retain endotracheal tube 50 within channel 49 of member 40. This embodiment also includes a bite blade 52 extending from bite plate 46 generally parallel with and spaced apart from tie plate 44. The bite blade 52 is a ridge fitting in the alveolar ridge between the patient's teeth and gums and his lips, thereby relieving any pressure against the mouth and cheek.

To use the invention, the patient is usually placed in a horizontal position, the patient's mouth is cleared of any foreign matter, the endotracheal tube is appropriately inserted in the tracheal lumen, the block is inserted so that the bite plate is between the teeth adjacent to the inside of the cheek, with the tie plate hugging the outside of the cheek, and the band is wrapped around the tube to secure it to the block. Then, the head strap is placed around the head and neck positioned so that the tube and block protrude partially through the appropriate section of the opening in the head strap. The head strap is then securely fastened around the head, being careful to check that the patient's lips are not bound into an improper position.

There are many advantages to this invention. First, the invention can retain any adult size endotracheal tube firmly and in the proper position within the patient's mouth, regardless of most unintentional movements by the patient. Second, the use of tape is entirely avoided, thereby eliminating the skin irritations that frequently occur with tape. Third, accidental occlusion or perforation of the tube by the patient's teeth is avoided. Fourth, the endotracheal tube can be properly positioned, secured, and if necessary, repositioned easily and quickly. Of course, other advantages of the invention will be apparent to those skilled in the art.

While the principles of the invention have been described above in connection with specific apparatus and applications, it is to be understood that this description is made only by way of example and not as a limitation on the scope of the invention.

We claim:

1. A device for holding an endotracheal tube comprising:
    a tie plate curved to rest along the outside of a patient's cheek, said tie plate having a first tie-plate end;
    a bite plate curved to extend along the inside of a patient's cheek and between a patient's upper and lower gums, said bite plate having a first bite-plate end;

a member connecting said first tie-plate end with said first bite-plate end so as to form a channel between them, said tie plate and bite plate adapted to grip a patient's cheek in the channel between them so as to maintain said tie plate, said bite plate and said member in a fixed position in a patient's mouth, said tie plate, said bite plate and said member sized and shaped to extend only about half-way across a patient's mouth so as to permit access to a patient's mouth cavity while said device is in the patient's mouth;

means for securing an endotracheal tube to said member, said bite plate having a width sufficiently greater than said tube to prevent a patient from biting said tube; and means for securely fixing and holding said member tie plate, bite plate and securely in patient's mouth.

2. The device of claim 1 wherein said securing means comprises:

a channel contoured to receive said tube, said channel being defined in said member;

at least one projection extending from said member; and a band connected to said member having a plurality of apertures therein, said band adapted to extend around the tube and to be held tightly against the tube by hooking said apertures on said projection.

3. The device of claim 2 wherein said band comprises an elastic non-skid material.

4. The device of claim 2 wherein said band comprises a latex material.

5. The device of claim 2 wherein said band includes a plurality of apertures.

6. The device of claim 5 wherein said apertures are co-linear.

7. The device of claim 1 wherein said means for fixing and holding said member in patient's mouth comprises:

a strap having one end connected to a second end of said tie plate, said strap adapted to extend around the head of a patient;

a plurality of hooks secured at an opposite end of said strap;

a plurality of loops secured adjacent the one end of said strap, said hooks and loops forming a fastener permitting securing said strap tightly around patient's head.

8. The device of claim 1 wherein said securing means comprises two projections extending from opposite sides of said member and an elastic band having a plurality of apertures therein, said band adapted to extend around the tube and be secured to said member by said projections piercing through said apertures.

9. The device of claim 1 wherein the means for fixing and holding comprises an elastic strap which surrounds the patient's head and neck, said strap including an opening located in a medial portion of the strap to permit passage of an endotracheal tube, and releasable fastener means for adjusting the diameter of said strap to correspond to the diameter of a patient's head and neck.

10. A device for holding an endotracheal tube comprising:

a tie plate curved to rest along the outside of a patient's cheek, said tie plate having a first tie plate and;

a bite plate curved to extend along the inside of a patient's cheek and between a patient's upper and lower gums, said bite plate having a first bite-plate end;

a member connecting said first tie-plate end with said first bite-plate end so as to form a channel between them, said tie plate and bite plate adapted to grip the patient's cheek in the channel between them so as to maintain said tie plate, said bite plate and said member in a fixed position in a patient's mouth, said tie plate, said bite plate and said member being sized and shaped to extend only part way across the patient's mouth so as to permit access to a patient's mouth cavity while said device is in the patient's mouth;

means for securing an endotracheal tube to said member, said bite plate having a width sufficiently greater than said tube to prevent a patient from biting said tube; and means for fixing and holding said tie plate, bite plate and member securely in patient's mouth, said bite plate being tapered toward the end away from said member to form a wedge for prying open a patient's mouth by pushing said wedge between patient's lower and upper teeth.

11. The device of claim 10 wherein said securing means comprises:

a channel contoured to receive said tube, said channel being defined in said member;

at least one projection extending from said member; and a band connected to said member having a plurality of apertures therein, said band adapted to extend around the tube and to be held tightly against the tube by hooking said apertures on said projection.

12. The device of claim 11 wherein said band comprises an elastic non-skid material.

13. The device of claim 11 wherein said band comprises a latex material.

14. The device of claim 11 wherein said band includes a plurality of apertures.

15. The device of claim 14 wherein said apertures are co-linear.

16. The device of claim 10 wherein said means for fixing and holding said member in patient's mouth comprises:

a strap having one end connected to a second end of said tie plate, said strap adapted to extend around the head of a patient;

a plurality of hooks secured at an opposite end of said strap;

a plurality of loops secured adjacent the one end of said strap, said hooks and loops forming a fastener permitting securing said strap tightly around patient's head.

17. The device of claim 10 wherein said securing means comprises two projections extending from opposite sides of said member and an elastic band having a plurality of apertures therein, said band adapted to extend around the tube and be secured to said member by said projections piercing through said apertures.

18. The device of claim 10 wherein the means for fixing and holding comprises an elastic strap which surrounds the patient's head and neck, said strap including an opening located in a medial portion of the strap to permit passage of an endotracheal tube, and releasable fastener means for adjusting the diameter of said strap to correspond to the diameter of a patient's head and neck.

19. A method of securing an endotracheal tube within a patient's mouth using an endotracheal tube retainer as defined in claim 10 which includes a tapered bite plate and a tie plate substantially parallel to said bite plate, said method comprising:
- (a) inserting the endotracheal tube within the patient's tracheal lumen;
- (b) wedging the patient's mouth open by pushing between upper and lower teeth of the patient said tapered bite plate of said endotracheal tube retainer and as the patient's mouth opens continuing to push said tube retainer toward one corner of patient's mouth until said bite plate and said tie plate grip the patient's cheek;
- (c) securing said endotracheal tube to said tube retainer; and
- (d) attaching the tube securing means to the patient's head and/or neck.

20. The method of claim 19 wherein step (c) comprises wrapping the endotracheal tube with an elastic band attached at its ends to the tube securing means.

21. The method of claim 20 wherein step (d) comprises encircling the patient's head and/or neck with an elastic strap and tieing said tube receiving means to said strap.

* * * * *

UNITED STATES PATENT AND TRADEMARK OFFICE
CERTIFICATE OF CORRECTION

PATENT NO. : 4,326,515
DATED : April 27, 1982
INVENTOR(S) : Mark Shaffer and Frank Baker It is certified that error appears in the above-identified patent and that said Letters Patent is hereby corrected as shown below:

On the title page, first line of the Denmark Patent "928035" should read -- 92803 --.

Signed and Sealed this

Third Day of August 1982

[SEAL]

Attest:

Attesting Officer

GERALD J. MOSSINGHOFF
Commissioner of Patents and Trademarks